United States Patent [19]
Sutton

[11] Patent Number: 4,617,926
[45] Date of Patent: Oct. 21, 1986

[54] DEPILATION DEVICE AND METHOD

[76] Inventor: A. Gunilla Sutton, 19, Tregunter Road, London SW10, United Kingdom

[21] Appl. No.: 574,922

[22] Filed: Jan. 30, 1984

[51] Int. Cl.⁴ .............................................. A61N 5/00
[52] U.S. Cl. .................. 128/303.1; 128/355; 128/398; 350/96.1; 350/96.18
[58] Field of Search ...................... 128/303.1, 395–398, 128/355; 219/121 LA; 350/96.1, 96.18, 96.29, 96.30, 96.32

[56] References Cited

U.S. PATENT DOCUMENTS

| | | | |
|---|---|---|---|
| 3,404,350 | 10/1968 | Muncheryan | 219/121 LA |
| 3,538,919 | 11/1970 | Meyer | 128/398 |
| 3,693,623 | 9/1972 | Harte et al. | 128/398 |
| 3,712,986 | 1/1973 | Collings | 350/96.29 X |
| 3,834,391 | 9/1974 | Block | 128/303.1 |
| 3,843,865 | 10/1974 | Nath | 128/395 X |
| 3,999,552 | 12/1976 | Huggins | 128/303.13 |
| 4,388,924 | 6/1983 | Weissman et al. | 128/303.1 |

FOREIGN PATENT DOCUMENTS

| | | | |
|---|---|---|---|
| 1041610 | 10/1978 | Canada | 128/303.1 |

*Primary Examiner*—Lee S. Cohen
*Attorney, Agent, or Firm*—Ralph R. Rath

[57] ABSTRACT

A depilation device includes a laser beam generator 15 embodied in a hand gun 20 with a trigger 19 enabling pulses of laser energy to be delivered along a flexible fibre optic probe 13 which has a bore in the end which can fit over a hair to be destroyed. At the end of the bore, the optic is formed as a convex lens so that the pulses of energy are focused into the hair so that the hair and follicle can be destroyed without destroying surrounding tissue.

12 Claims, 2 Drawing Figures

DEPILATION DEVICE AND METHOD

TECHNICAL FIELD

This invention relates to a depilation device, and one object is to provide such a device which enables the user quite easily and safely to destroy unwanted hairs without requiring expensive apparatus.

SUMMARY OF THE INVENTION

According to the present invention, a depilation device comprises a flexible fibre optical probe with a bore at its tip to accommodate a hair; in one embodiment, there is a lens within the bore to focus energy in the probe into the hair. In another embodiment, the probe is of small external diameter and has a sharpened tip to assist in penetrating the follicle itself.

By applying the tip of the probe over the hair, a path is established for laser beam (or possible other type) energy to be applied as a pulse to the root of the hair or follicle, thus preventing regrowth.

The bore may extend from the tip of the probe for a distance equal to the length of a cut-off hair, or perhaps two or three millimeters (mm), and then in the one embodiment mentioned above, the lens may be formed as a convex-ended closure to the bore so that it acts as a lens to focus the energy, thus restricting the energy to flow within the hair to its follicle so as not to cause damage to surrounding tissues.

As human and mammalian hairs vary in thickness considerably, a selection of detachable probes will be necessary with different convergent lenses offering a range of focal lengths to accommodate the variation in depth of hair follicles. The external diameter of a probe could be 3 mm and internal diameters could range from 0.3 mm to 1 mm.

The invention includes the flexible fibre optical probe connected to the output from a laser beam generator which is connected to a pulse-forming circuit and a trigger with which to fire when the probe is in position and the hair is to be destroyed. Those components can conveniently be mounted in a hand gun equipped with a battery of commonly available type, to act as a power source for the laser beam generator.

This device has application in human dermatological therapy (including treatment of naevus and related conditions), cosmetic therapy and as veterinary treatments.

BRIEF DESCRIPTION OF SEVERAL VIEWS OF DRAWINGS

FIG. 1 is a side elevational view partly in section, showing a depilation device constructed in accordance with the teachings of the present invention; and, FIG. 2 is a view similar to FIG. 1 showing a slightly modified form of the invention.

DETAILED DESCRIPTION

Figure 1:
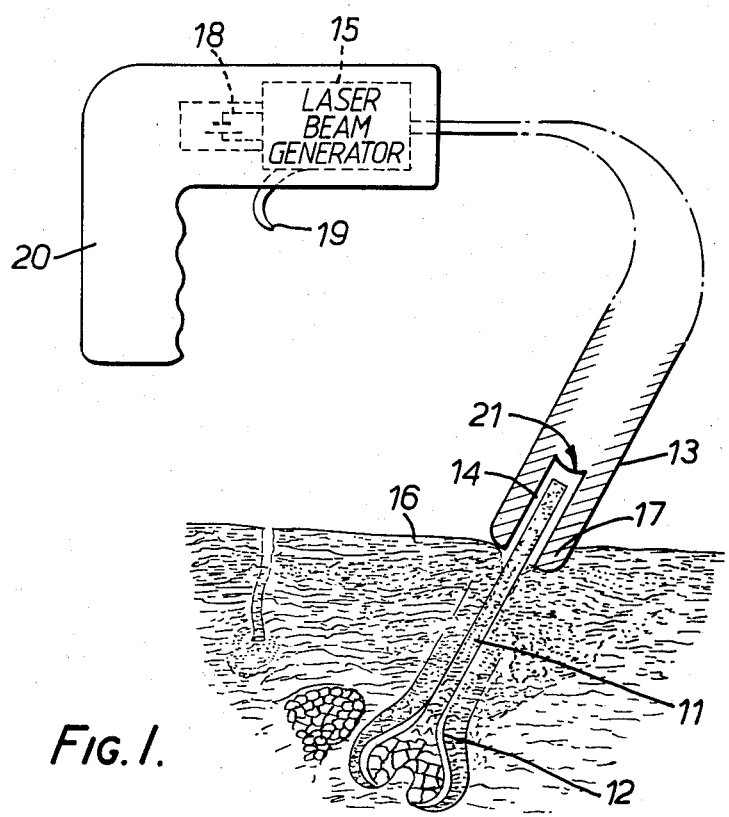

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated.

Figure 2:
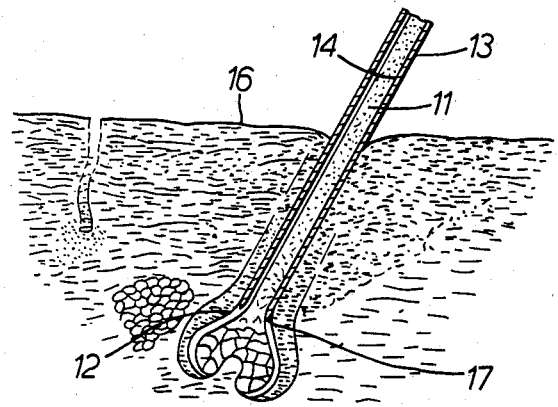

The invention may be carried into practice in various ways, but two embodiments are illustrated in FIGS. 1 and 2.

In FIG. 1, the hair 11 and its follicle 12 are to be destroyed and for that purpose a flexible fibre optic probe 13 of approximately 3 mm external diameter is used. It has a central longitudinal bore 14 at its tip, about 2 mm to 3 mm long, of 0.3 mm to 1 mm internal diameter.

A convex lens 21 is defined at the end of the bore.

At one end, the probe 13 is connected to the discharge of a laser beam generator 15 so that light from the laser beam is conducted along the coaxial glass body of the probe to the lens 21. It is focused into the end of the hair and is conducted along the hair to the follicle where the energy is dissipated resulting in destruction of the follicle without damage to surrounding tissues.

The generator 15 is powered by a battery cell 18 connected through a pulse-forming circuit (not shown) to the laser beam generator 15 and when the trigger 19 is pressed, a pulse of radiation is generated and transmitted along the probe to be focused into the hair and its follicle in order to destroy them.

The components are conveniently housed in a pistol-like body 20 housing the trigger 19.

It is anticipated that the energy necessary to destroy a hair (or a naevus or related dermatological conditions) might be approximately one joule so that a small battery can be effective for destroying a large number of hairs, etc. The user merely applies the end of the probe to the hair (or naevus, etc.) to be removed and presses the trigger.

For particularly resilient hairs, the alternative probe 13 of FIG. 2 is positioned over the hair 11, penetrating the skin 16 using the hair 11 to guide the probe 13 into the follicle 12.

The flexible probe may have an external diameter of 1 mm to 1.5 mm with an internal bore of about 0.3 mm to 1 mm diameter. The tip is sharpened as shown at 17 to assist penetration of the follicle.

Pulsed energy is delivered directly into the follicle through the central longitudinal bore 14 to destroy the hair. No convergent lens such as 21 is required.

The generator and pistol are as in FIG. 1.

I claim:

1. A depilation device comprising a probe having an optic fiber with a bore in the tip of the fiber, said bore being of a size for accommodating a hair therein so that energy transmitted through the optic fiber will impinge directly on the hair.

2. A depilation device comprising a probe having an optic fiber with a bore in its tip with a diameter of between 0.3 mm and 1 mm and a length for accommodating a hair.

3. A depilation device as claimed in claim 1 or claim 2, including a lens within the bore for focusing energy in the probe into the hair.

4. A device as claimed in claim 1 or claim 2, including a convex lens formed at the end of the bore for focusing energy in the probe into the hair.

5. A device as claimed in claim 1 or claim 2 in which the bore extends from the tip of the probe for a distance of about 2-3 mm.

6. A device as claimed in claim 1 or claim 2, in which the external diameter of the probe is no more than 3 mm.

7. A device as claimed in claim 1 or claim 2, in which the external diameter of the probe is in the range of about 1.0 mm to 1.5 mm.

8. A device as claimed in claim 1 or claim 2 in which the tip of the probe is sharp.

9. A depilation device as claimed in claim 1 or claim 2, including a light energy pulse-forming circuit and a trigger connected in the circuit with which the circuit can be fired, and in which the fiber optic probe is connected to the pulse-forming circuit.

10. A depilation device comprising in combination a hand gun, a light energy pulse-forming circuit housed in the gun with a trigger connected in the circuit for firing the circuit, and an optic fiber probe with a bore in the tip of the fiber of a size for accommodating a hair therein, the probe being connected to receive the energy pulse formed in the circuit.

11. A method of destroying an unwanted mammalian hair by applying a pulse of light energy by means of an optic fiber into the end of the hair, along the hair and hence into the hair follicle to destroy the follicle.

12. A method of destroying an unwanted mammalian hair by applying a fiber optic probe to the hair with the hair extending into a bore in the end of the probe, generating a pulse of light energy, and applying the pulse of energy to the probe, and hence into the end of the hair within the bore, and into the hair follicle, destroying the follicle.

* * * * *